(12) United States Patent
Le Prado et al.

(10) Patent No.: US 11,931,152 B2
(45) Date of Patent: Mar. 19, 2024

(54) SUPPORT HELMET FOR MAGNETOENCEPHALOGRAPHY DEVICE

(71) Applicant: Commissariat à l'Energie Atomique et aux Energies Alternatives, Paris (FR)

(72) Inventors: Matthieu Le Prado, Grenoble (FR); Etienne Labyt, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 266 days.

(21) Appl. No.: 17/753,129

(22) PCT Filed: Aug. 13, 2020

(86) PCT No.: PCT/EP2020/072807
§ 371 (c)(1),
(2) Date: Feb. 19, 2022

(87) PCT Pub. No.: WO2021/037584
PCT Pub. Date: Mar. 4, 2021

(65) Prior Publication Data
US 2022/0395208 A1 Dec. 15, 2022

(30) Foreign Application Priority Data
Aug. 30, 2019 (FR) ...................................... 1909583

(51) Int. Cl.
*A61B 5/245* (2021.01)
*A61B 5/00* (2006.01)
(Continued)

(52) U.S. Cl.
CPC ............ *A61B 5/245* (2021.01); *A61B 5/6803* (2013.01); *G01R 33/26* (2013.01); *A61B 2562/0223* (2013.01); *A61N 2/006* (2013.01)

(58) Field of Classification Search
CPC ........ A61N 2/006; A61B 5/245; A61B 5/6803
See application file for complete search history.

(56) References Cited

U.S. PATENT DOCUMENTS

| | | | |
|---|---|---|---|
| 2007/0225585 A1 | 9/2007 | Washbon et al. | |
| 2009/0088619 A1* | 4/2009 | Turner | A61B 5/291 600/587 |

(Continued)

FOREIGN PATENT DOCUMENTS

| | | |
|---|---|---|
| CN | 108670250 A | 10/2018 |
| EP | 0595227 A1 | 5/1994 |

OTHER PUBLICATIONS

International Search Report for International Application No. PCT/EP2020/072807 dated Sep. 24, 2020, 3 pages.

(Continued)

*Primary Examiner* — Carolyn A Pehlke
(74) *Attorney, Agent, or Firm* — Jordan IP Law LLC

(57) ABSTRACT

The present description concerns a support helmet (130) for a medical imaging or treatment device, comprising a head cap (131) provided with a plurality of through openings (133), each opening being adapted to receiving an elementary imaging or treatment module (110) assembled in the opening so as to slide along an axis substantially orthogonal to the head cap.

6 Claims, 3 Drawing Sheets

(51) Int. Cl.
   *G01R 33/26*   (2006.01)
   *A61N 2/00*    (2006.01)

(56)           References Cited

U.S. PATENT DOCUMENTS

2012/0226127 A1    9/2012   Asjes et al.
2014/0051960 A1*   2/2014   Badower .............. A61B 5/0006
                                                      600/383
2014/0121491 A1    5/2014   Zhang
2015/0257673 A1    9/2015   Lawrence et al.
2015/0282760 A1*  10/2015   Badower .............. A61B 5/6803
                                                      600/383
2016/0354005 A1*  12/2016   Oakley ................ A61B 5/6803
2017/0123495 A1    5/2017   Leuthardt et al.
2017/0258400 A1*   9/2017   Jovanovic ............. A61B 5/291
2017/0367650 A1*  12/2017   Wallois .................. G06F 3/015

OTHER PUBLICATIONS

Preliminary Search Report for French Application No. 1909583 dated Jan. 23, 2020, 4 pages.
Translation of the IPRP for International Application No. PCT/EP2020/072807, 6 pages.

* cited by examiner

SUPPORT HELMET FOR MAGNETOENCEPHALOGRAPHY DEVICE

FIELD

The present disclosure generally relates to magnetoencephalography devices and more particularly aims at a support helmet for a magnetoencephalography device, and a magnetoencephalography device comprising such a helmet.

BACKGROUND

A magnetoencephalography device aims at acquiring an image of the magnetic fields generated by the brain.

Existing magnetoencephalography devices use SQUID-type (Superconducting QUantum Interference Device) magnetometers. Such magnetometers are bathed in a cryogenic fluid. This results in a significant bulk and in a lack of modularity of the device. In particular, in existing magnetoencephalography devices, the magnetometers have a fixed position relative to a support helmet where the user places their head during an image acquisition phase. The helmet is generally provided to be adapted to the largest heads. In practice, the user's head may thus be several centimeters away from the edges of the helmet, and thus from the magnetometers. The fields measured by the magnetometers are thus attenuated, which degrades the quality of the acquired images.

It has recently been provided, as an alternative to SQUID-type magnetometers, to use optical pumping magnetometers. Optical pumping magnetometers indeed do not need being cooled by a cryogenic fluid, which enables to form less bulky and less expensive magnetoencephalography devices.

It would be desirable to at least partly improve certain aspects of magnetoencephalography devices based on optical pumping magnetometers.

SUMMARY

For this purpose, an embodiment provides a support helmet for a medical imaging or treatment device, comprising a head cap provided with a plurality of through openings, each opening being adapted to receiving an elementary imaging or treatment module assembled in the opening so as to slide along an axis substantially orthogonal to the head cap.

According to an embodiment, the helmet further comprises a tightening device adapted to exerting on each module a pressure towards the inside of the head cap, to hold the module against a user's head.

According to an embodiment, the tightening device comprises a lace capable of freely sliding in a passage provided for this purpose on each module.

According to an embodiment, the tightening device further comprises, fastened on the head cap, at least one self-locking element for tightening the lace.

According to an embodiment, the tightening device comprises an inflatable cushion located outside of the head cap.

According to an embodiment, the tightening device further comprises a shell located outside of the head cap, the inflatable cushion being located between the head cap and the shell.

According to an embodiment, the head cap is made of a rigid material.

According to an embodiment, the head cap comprises, at the level of an edge of each opening, a pin for guiding the elementary module, intended to cooperate with a corresponding guiding groove of the elementary module.

Another embodiment provides a medical imaging or treatment device, comprising a support helmet such as defined here above and a plurality of elementary imaging or treatment modules respectively assembled in the openings of the head cap of the helmet.

According to an embodiment, the elementary modules are optical pumping magnetometers.

BRIEF DESCRIPTION OF THE DRAWINGS

The foregoing features and advantages, as well as others, will be described in detail in the following description of specific embodiments given by way of illustration and not limitation with reference to the accompanying drawings, in which.

DETAILED DESCRIPTION OF THE PRESENT EMBODIMENTS

Like features have been designated by like references in the various figures. In particular, the structural and/or functional features that are common among the various embodiments may have the same references and may dispose identical structural, dimensional and material properties.

For the sake of clarity, only the steps and elements that are useful for an understanding of the embodiments described herein have been illustrated and described in detail. In particular, the inner structure of the optical pumping magnetometers of the described devices has not been detailed, the described embodiments being compatible with most known optical pumping magnetometer structures. Further, the peripheral control and processing circuits coupled to the optical pumping magnetometers of the described devices have not been detailed, the described embodiments being compatible with the control and processing circuits usually provided in magnetoencephalography devices based on optical pumping magnetometers, or the forming of these circuits being within the abilities of those skilled in the art.

Unless specified otherwise, when reference is made to two elements connected together, this signifies a direct connection without any intermediate elements other than conductors, and when reference is made to two elements coupled together, this signifies that these two elements can be connected or they can be coupled via one or more other elements.

In the following description, when reference is made to terms qualifying absolute positions, such as "front", "rear", "top", "bottom", "left", "right", etc., or relative positions, such as terms "above", "under", "upper", "lower", etc., or to terms qualifying directions, such as terms "horizontal", "vertical", etc., unless specified otherwise, it is referred to the orientation of the drawings or to a device in a normal position of use.

Unless specified otherwise, the expressions "around", "approximately", "substantially" and "in the order of" signify within 10%, and preferably within 5%.

Figure 1:
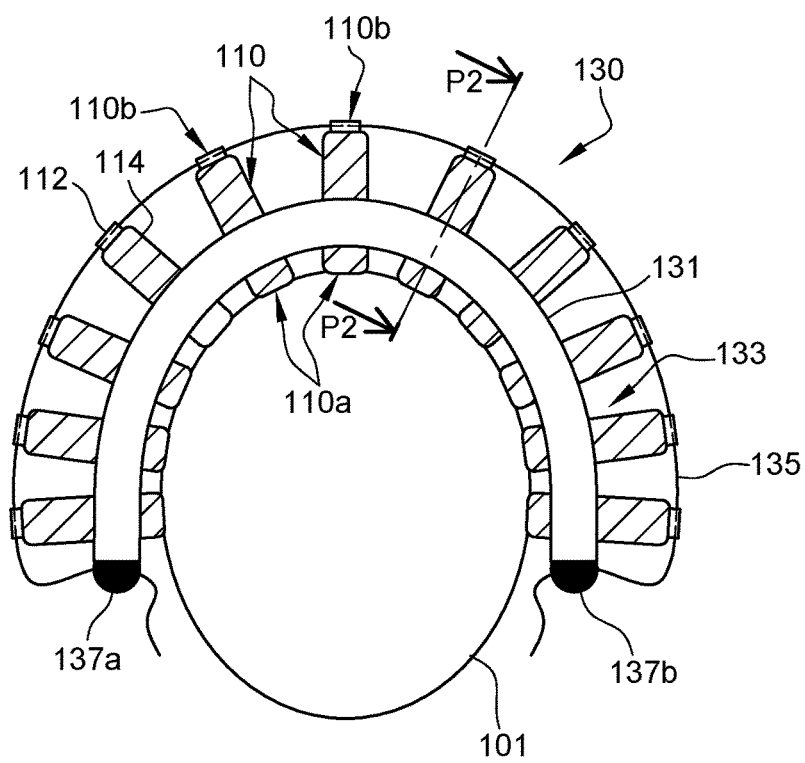
FIG. 1 schematically and partially shows an example of a magnetoencephalography device based on optical pumping magnetometers according to an embodiment.

FIG. 1 schematically and partially shows an example of a magnetoencephalography device based on optical pumping magnetometers according to an embodiment.

The device of FIG. 1 comprises a support helmet 130, having a plurality of elementary optical pumping magnetometers 110, for example, identical or similar to within manufacturing dispersions, fastened thereto. As an example, the device comprises from 20 to 200 elementary magnetometers 110. Magnetometers 110 are for example regularly distributed, with a constant pitch, on the surface of the helmet.

The support helmet 130 of the device of FIG. 1 comprises a head cap 131 intended to be placed on a user's head 101. Head cap 131 may have a bulged shape, for example, the shape of a sphere or ellipsoid portion. Head cap 131 is provided with a plurality of through openings 133, for example, substantially of same dimensions, each opening being capable of receiving an elementary magnetometer 110. Head cap 131 may be made of a rigid material, for example, of plastic.

Each elementary magnetometer 110, once placed in an elementary opening 133 of head cap 131, has a first surface 110a located inside of the head cap, facing the user's head, and a second surface 110b opposite to surface 110a, located outside of the head cap.

Each magnetometer 110 is capable of sliding in the corresponding opening 133 of head cap 131, along an axis substantially orthogonal to the head cap. More particularly, in this example, each magnetometer may displace in opening 133 according to a single degree of liberty in translation along an axis substantially orthogonal to the head cap. Axis substantially orthogonal to the head cap here means an axis forming an angle smaller than 30 degrees, and preferably smaller than 20 degrees, in absolute value, with the axis normal to the outer surface of the head cap at the level of the center of opening 133.

As an example, magnetometers 110 have, in transverse cross-section, that is, along a plane substantially orthogonal to their sliding axis, a shape substantially identical to that of openings 133. The dimensions of openings 133 may be very slightly greater than those of the magnetometers to allow the passage of magnetometers through the openings. This enables to authorize a shifting of magnetometers 110 along their longitudinal axis, while blocking shifting motions in the other directions. As an example, the dimensions of openings 133 are greater by from 1 to 5% than the transverse dimensions of magnetometers 110. As an example, in top view, the dimensions of openings 133, substantially corresponding to the transverse dimensions of magnetometers 110, are in the range from 10 to 40 millimeters, for example, in the order of 20 millimeters.

Magnetometers 110 for example have a generally parallelepipedal shape, for example, cuboid. More generally, magnetometers 110 may have any shape, for example, a cylindrical shape.

In this example, magnetometers 110 may slide independently from one another along their respective sliding axes. In other words, magnetometers 110 are not mechanically fastened to one another.

The support helmet 130 of FIG. 1 further comprises a tightening device adapted to applying on each magnetometer 110 a pressure towards the inside of the head cap, parallel to its sliding axis, to hold surface 110a of the magnetometer bearing against the user's head, for example, in contact with the user's head.

In the example of FIG. 1, the tightening device comprises a lace 135 adapted to freely sliding in a passage or guide provided for this purpose on each magnetometer 110. In the shown example, each magnetometer 110 comprises, on the side of its surface 110b opposite to the user's head, a passage duct 112 fastened on a protection package 114 of the magnetometer, lace 135 running through the respective ducts of the different magnetometers. Lace 135 is for example elastic.

In the example of FIG. 1, the tightening device further comprises two self-locking elements 137a and 137b for tightening lace 135. In this example, self-locking tightening elements 137a and 137b are attached to an edge of head cap 131, respectively on the left-hand side and on the right-hand side of the user's head. Lace 135 has a first end held by tightening element 137a and a second end held by tightening element 137b. The tightening of lace 135 by means of elements 137a and 137b enables to apply to the different magnetometers 110 a pressure capable of holding the surface 110a of each magnetometer bearing against the user's skull, for example in contact with the user's head.

In practice, the elementary magnetometers may be arranged along a plurality of rows of a plurality of magnetometers each. The tightening device may comprise one lace 135 per row of magnetometers. The different laces 135 for example run through the same two self-locking tightening elements 137a and 137b. As a variant, the tightening device comprises a single self-locking tightening element fastened to head cap 131, each lace 135 having a first end directly fastened to the head cap and having a second end held by the self-locking tightening element. As a variant, different laces are held by distinct self-locking tightening elements. The laces are for example distributed into a plurality of groups of one or a plurality of laces per group, the tightening device comprising, fastened to the head cap, one or two self-locking tightening elements per group of laces.

Figure 2:
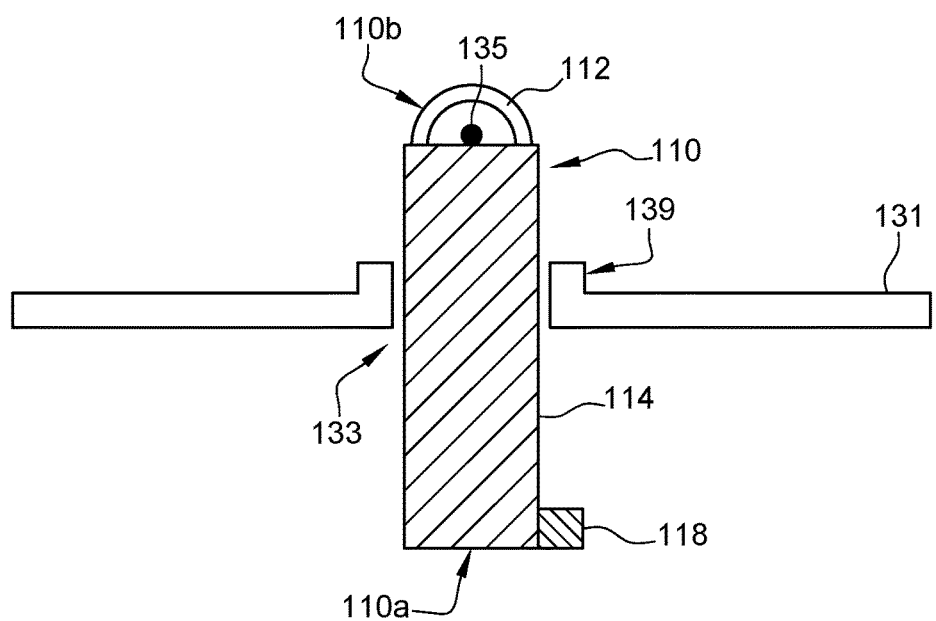
FIG. 2 is a more detailed cross-section view of a portion of the device of FIG. 1.

FIG. 2 is a more detailed cross-section view of a portion of the device of FIG. 1, along plane P2 of FIG. 1. In FIG. 2, a single magnetometer 110 is shown, as well as a corresponding portion of head cap 131.

As shown in FIG. 2, in this example, head cap 131 comprises, at the edge of each opening 133, a shoulder 139 (not shown in FIG. 1) particularly enabling to ease the guiding of magnetometer 110. As an example, shoulder 139 forms, at the periphery of opening 133, a raised area protruding from the outer surface of head cap 131. As an example, in top view, shoulder 139 entirely surrounds opening 133. In the shown example, the inner edge of shoulder 139 is stacked to the edge of opening 133. As an example, shoulder 139 has a thickness in the range from 5 to 25 millimeters, for example, in the order of 10 millimeters, in addition to the thickness of head cap 131.

Figure 3:
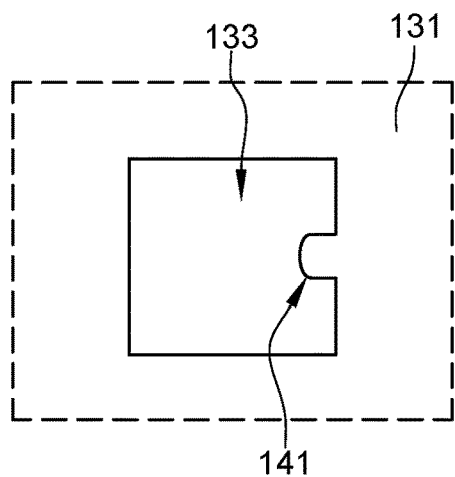
FIG. 3 is a bottom view of a portion of a support helmet of the device of FIG. 1.

FIG. 3 is an enlarged bottom view of a portion of the head cap 131 of the device of FIG. 1. In FIG. 3, a single opening 133 has been shown.

Figure 4:
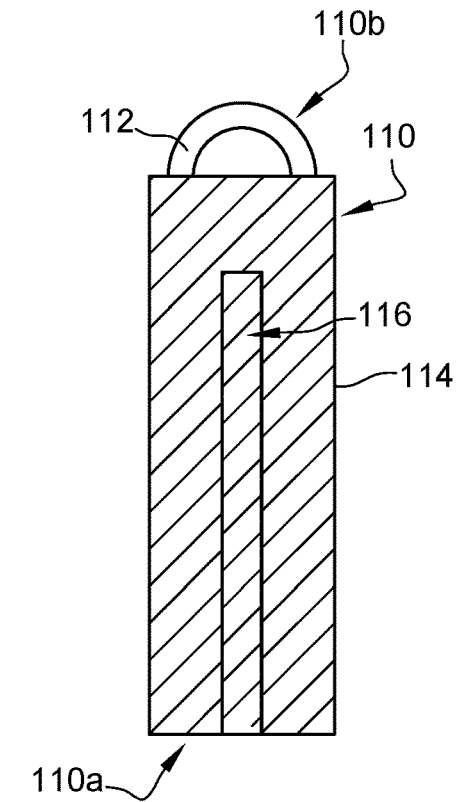
FIG. 4 is a lateral view of an elementary magnetometer of the device of FIG. 1.

FIG. 4 shows an enlarged lateral view of an elementary magnetometer 110 of the device of FIG. 1.

Figure 5:
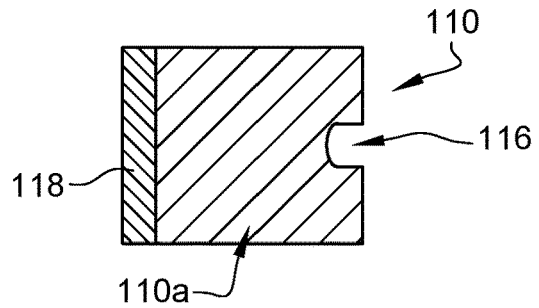
FIG. 5 is a bottom view of an elementary magnetometer of the device of FIG. 1.

FIG. 5 illustrates a bottom view of the elementary magnetometer 110 of FIG. 4.

As shown in FIG. 3, head cap 131 may comprise, at each opening 133, a guide pin 141 protruding from an edge of the opening. Each elementary magnetometer 110 may comprise, on a lateral surface, a guiding groove or recess 116 (FIGS.

4 and 5), extending on all or part of the length of the magnetometer, in the magnetometer sliding direction. Pin 141 is intended to cooperate with groove 116 to ensure the guiding of the magnetometer in opening 133. Pin 141 and groove 116 are further used as a key to set the orientation of magnetometer 110 with respect to the head cap. As an example, groove 116 extends from the lower surface 110a of the magnetometer, along a portion only of the height of the magnetometer, for example, along from 50 to 90% of the height of the magnetometer. The interruption of groove 116 before the upper surface 110b of the magnetometer enables to form an abutment avoiding for the magnetometer to fall into head cap 131, for example, when the user's head is not present in the helmet. The extension of groove 116 all the way to the lower surface 110a of the magnetometer enables to insert the magnetometer into opening 133, from the upper surface of head cap 131.

As shown in FIGS. 2 and 5, each elementary magnetometer 110 may further comprise, on one of its lateral surfaces, for example, its surface opposite to groove 116, in the vicinity of its lower surface 110a, a shoulder 118 removably fastened to magnetometer package 114, for example, by means of a screw or of a snap fastening system. Shoulder 118 is used as an abutment enabling to avoid for the magnetometer to come out on the outer surface side of head cap 131, for example if the helmet is turned over. Shoulder 118 is removably attached to enable its removal on insertion of magnetometer 110 into opening 133 or on removal of magnetometer 110 from opening 133.

It should be noted that the described embodiments are not limited to the specific examples of guiding mechanism and of abutment described hereabove. More generally, all other mechanisms adapted to ensuring the above-described functions may be used. For example, fixed pin 141 may be replaced with a spring-loaded retractable pin. Similarly, shoulder 118 may be replaced with a spring-loaded retractable pin.

Although this has not been shown, the magnetoencephalography device of FIG. 1 may further comprise a central control and processing circuit coupled to the optical pumping magnetometers 110, for example, by wire link or by radio link.

An advantage of the magnetoencephalography device of FIG. 1 is that it enables to apply the magnetometers at closest to the user's head, whatever the size thereof.

Further, since the magnetometers are removably fastened to the support helmet, and due to the relatively low cost of the support helmet, a plurality of different helmet sizes may be provided, for example, from 3 to 4 helmet sizes, to adapt to different ranges of head dimensions (for example, a baby size, a child size, and an adult size).

Further, the magnetometers being removably fastened to the support helmet, the number of magnetometers and their position on the helmet may be adapted according to the measurement which is desired to be performed. Thus, during a measurement, certain openings 133 of head cap 131 may remain free, that is, non-equipped with a magnetometer.

Figure 6:
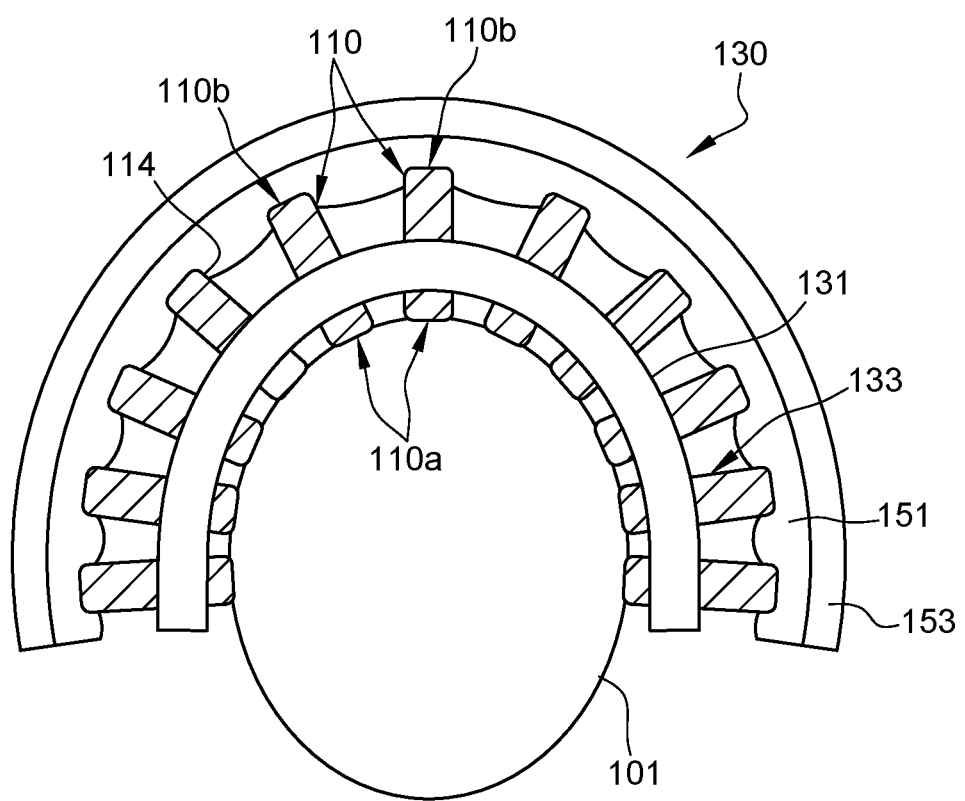
FIG. 6 schematically and partially shows an alternative embodiment of the magnetoencephalography device of FIG. 1.

FIG. 6 schematically and partially shows an alternative embodiment of the magnetoencephalography device of FIG. 1.

The device of FIG. 6 differs from the device of FIG. 1 mainly by the nature of the tightening device used to apply, on each elementary magnetometer 110, a pressure towards the inside of the head cap, enabling to hold surface 110a of the magnetometer bearing against the user's head.

In the example of FIG. 6, the tightening device comprises an inflatable cushion 151, for example, an air cushion, located outside of head cap 131. The tightening device of FIG. 6 further comprises an outer shell 153 located outside of head cap 131, on the side of inflatable cushion 151 opposite to head cap 131. Shell 153 is for example a rigid shell mechanically fastened to head cap 131. Inflatable cushion 151 has an inner surface bearing against the outer surfaces 110b of elementary magnetometers 110, and an outer surface bearing against an inner surface of outer shell 153. A pump, not shown, may be provided to adjust the pressure of air cushion 151 to hold magnetometers 110 bearing against the user's head. Preferably, the pump will then be placed outside of a magnetic shielding (not shown) provided to isolate magnetometers 110 from possible outer parasitic magnetic fields.

More generally, other tightening devices may be provided to ensure the holding of the magnetometers bearing against the user's head, for example spring-loaded devices.

Various embodiments and variants have been described. Those skilled in the art will understand that certain features of these various embodiments and variants may be combined, and other variants will occur to those skilled in the art. In particular, the described embodiments are not limited to the particular examples of dimensions mentioned in the present disclosure.

Further, although devices have been described here above for magnetoencephalography applications, these devices may be adapted to other applications of medical imaging or medical treatment of the brain or of the head, by replacing optical pumping magnetometers 110 with other elementary imaging or treatment modules. As an example, optical pumping magnetometers 110 may be replaced with other types of sensors, for example, optical, terahertz, acoustic, etc., or also by modules of elementary treatment and stimulation, for example, by means of radio waves or by means of a magnetic field.

What is claimed is:

1. Support helmet for a medical imaging or treatment device, comprising a head cap provided with a plurality of through openings, each opening being adapted to receiving an elementary imaging or treatment module assembled in the opening so as to slide along an axis substantially orthogonal to the head cap, the helmet further comprising a tightening device adapted to exerting on each module a pressure towards the inside of the head cap, to hold the module bearing against a user's head, wherein the tightening device comprises a lace adapted to freely sliding in a passage provided for this purpose on each module.

2. Helmet according to claim 1, wherein the tightening device further comprises, fastened on the head cap, at least one self-locking element for tightening the lace.

3. Helmet according to claim 1, wherein the head cap is made of a rigid material.

4. Helmet according to claim 1, wherein the head cap comprises, at the level of an edge of each opening, a pin for guiding the elementary module, intended to cooperate with a corresponding guiding groove of the elementary module.

5. Medical imaging or treatment device, comprising a support helmet according to claim 1, and a plurality of elementary imaging or treatment modules respectively assembled in the openings of the head cap of the helmet.

6. Imaging or treatment device according to claim 5, wherein the elementary modules are optical pumping magnetometers.

\* \* \* \* \*